United States Patent [19]

Felix

[11] 4,444,693

[45] Apr. 24, 1984

[54] METHOD FOR PREPARATION OF N-PHOSPHONOMETHYLGLYCINE

[75] Inventor: Raymond A. Felix, Richmond, Calif.

[73] Assignee: Stauffer Chemical Company, Westport, Conn.

[21] Appl. No.: 415,083

[22] Filed: Sep. 7, 1982

[51] Int. Cl.³ .................................................. C07F 9/38
[52] U.S. Cl. ............................. 260/502.5 F; 260/940; 260/944
[58] Field of Search .................. 544/214; 260/502.5 F

[56] References Cited

U.S. PATENT DOCUMENTS 4,197,254  4/1980  Gaertner ........................ 260/502.5 F Primary Examiner—Anton H. Sutto
Attorney, Agent, or Firm—Edwin H. Baker

[57] ABSTRACT

A method of preparing N-phosphonomethylglycine comprising: (a) reacting O,O-dialkylaminomethylphosphonate with formaldehyde to produce a triazine compound; (b) reacting the triazine formed in step (a) with an acyl cyanide to form the O,O-dialkyl-N-phosphonomethyl-N-cyanomethyl amide; and (c) hydrolyzing the amide formed in step (b) to yield N-phosphonomethylglycine.

7 Claims, No Drawings

METHOD FOR PREPARATION OF N-PHOSPHONOMETHYLGLYCINE

FIELD OF THE INVENTION

This invention is a new process for preparing N-phosphonomethylglycine.

BACKGROUND OF THE INVENTION

N-Phosphonomethylglycine and certain salts are particularly effective as post-emergence herbicides. The commercial herbicide is sold as a formulation containing the isopropylamine salt of N-phosphonomethylglycine.

N-Phosphonomethylglycine can be made by a number of methods. One such method, as described in U.S. Pat. No. 3,160,632 is to react N-phosphinomethylglycine (glycinemethylenephosphonic acid) with mercuric chloride in water at reflux temperature, and subsequently separating the reaction products. Other methods are phosphonomethylation of glycine and the reaction of ethyl glycinate with formaldehyde and diethylphosphite. The latter method is described in U.S. Pat. No. 3,799,758. In addition, there is a series of patents relating to the preparation of N-phosphonomethylglycine, including U.S. Pat. Nos. 3,868,407, 4,197,254 and 4,199,354.

Close prior art is U.S. Pat. No. 3,923,877, which teaches the reaction of 1,3,5-tricyanomethylhexahydro-1,3,5-triazine with excess disubstituted phosphite to form $(RO)_2P(O)CH_2NHCH_2CN$ (R is hydrocarbyl or substituted hydrocarbyl) which is hydrolyzed to yield N-phosphonomethylglycine.

Because of the commercial importance of N-phosphonomethylglycine and certain salts as herbicides, improved methods of preparing these compounds are valuable.

BRIEF DESCRIPTION OF THE INVENTION

This invention relates to a process for preparing N-phosphonomethylglycine which comprises:

(1) reacting O,O-dialkylaminomethylphosphonate with formaldehyde to produce N,N',N''-tris[O,O-dialkylphosphonomethyl]hexahydro-1,3,5-triazine;

(2) reacting the triazine with an acyl cyanide compound to form an O,O-dialkyl-N-phosphonomethyl-N-cyanomethyl-amide; and (3) hydrolyzing the amide to yield N-phosphonomethylglycine.

DETAILED DESCRIPTION OF THE INVENTION

The process of this invention may be illustrated by the following reaction scheme:

(a) 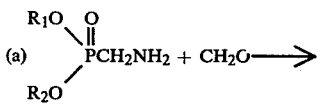

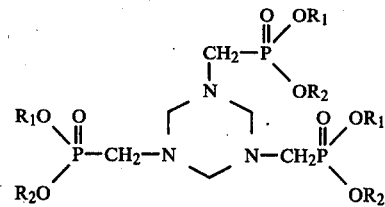

wherein $R_1$ and $R_2$ are both aromatic or aliphatic groups, preferably $R_1$ and $R_2$ are $C_1$–$C_6$ alkyl, more preferably $C_1$–$C_4$ alkyl, most preferably ethyl.

(b) 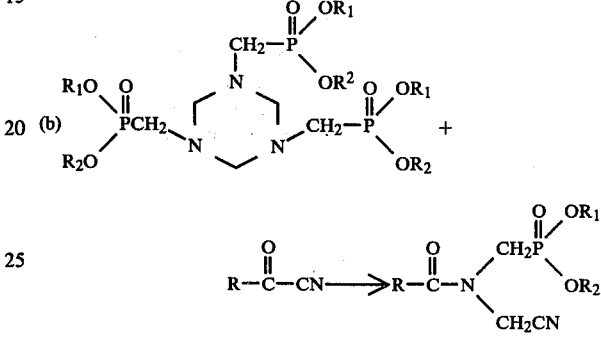

wherein R is an aliphatic or aromatic group as defined hereinafter, preferably phenyl or $C_1$–$C_4$ alkyl, and $R_1$ and $R_2$ are defined as above.

(c) 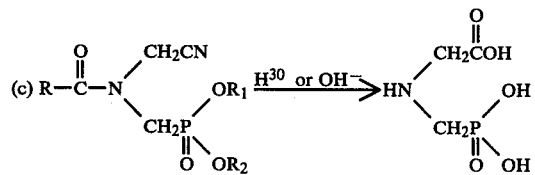

wherein R, $R_1$ and $R_2$ are as defined above and $H^+$ is a strong acid such as hydrochloric, hydrobromic, hydriodic, nitric, sulfuric, phosphonic or chloroacetic acid. Preferably $H^+$ is hydrochloric or hydrobromic acid and $OH^-$ is a strong base such as sodium hydroxide or potassium hydroxide, preferably in an aqueous, aqueous-alcoholic or alcoholic solution. Preferably, the hydrolysis is run in the presence of a strong acid.

In the above reaction scheme, the groups $R_1$ and $R_2$ are not directly involved in reaction step (a) between O,O-dialkylaminomethylphosphonate and formaldehyde. Groups R, $R_1$ and $R_2$ are not directly involved in reaction step (b) between N,N',N''-tris[O,O-dialkylphosphonomethyl]hexahydrotriazine and the acyl cyanide compound. Groups R, $R^1$ and $R^2$ are removed in reaction step (c) when the amide reaction product of reaction step (b) is subjected to hydrolysis. Therefore, the nature of groups R, $R^1$ and $R^2$ is not critical, although groups which would interfere with reaction steps (a) and (b) are to be avoided.

The group "$C_1$–$C_4$ alkyl" encompasses methyl, ethyl, n-propyl, isopropyl, n-butyl, isobutyl, sec-butyl, and tert-butyl. The group "$C_1$–$C_6$ alkyl" encompasses the same radicals as $C_1$–$C_4$ alkyl plus the 6 pentyls and the 16 hexyls.

The term "aliphatic group" is used in a broad sense to cover a large class of organic groups characterized by being derived from (1) an acylic (open-chain structure) of the paraffin, olefin and acetylene hydrocarbon series and their derivatives or (2) alicyclic compounds. The aliphatic group can have from 1 to 10 carbon atoms.

The term "aromatic group" is used in a broad sense to distinguish from the aliphatic group and includes a group derived from (1) compounds having 6 to 20 carbon atoms and characterized by the presence of at least one benzene ring, including monocyclic, bicyclic and polycyclic hydrocarbons and their derivatives and (2) heterocyclic compounds having 5 to 19 carbon atoms which are similar in structure and are characterized by having an unsaturated ring structure containing at least one atom other than carbon such as nitrogen, sulfur and oxygen and derivatives of these heterocyclic compounds.

Reaction step (a) is preferably run at a temperature between about 0° to about 100° C., more preferably between about 0° to about 30° C. This reaction step can be run at atmospheric, sub-atmospheric, or super-atmospheric pressure, preferably at atmospheric pressure. Preferably the reaction is run in a solvent for the phosphonate, such as dichloromethane, dichloroethane, toluene, or ether. One mole of formaldehyde is needed to react with one mole of O,O-diethylaminomethylphosphonate. An excess of formaldehyde can be used to insure complete reaction with the phosphonate.

Reaction step (b) is preferably run at a temperature between about 0° C. to about 150° C., more preferably between about 70° to about 90° C. This reaction step can be run at atmospheric, sub-atmospheric, or super-atmospheric pressure, preferably at atmospheric pressure. Preferably the reaction is run in a solvent for the acyl cyanide compound, such as ethylene dichloride, methylene chloride or toluene. Three moles of the acyl cyanide compound are needed to react with one mole of the N,N',N''-tris(O,O-dialkylphosphonomethyl)hexahydrotriazine; furthermore, an excess of the acyl cyanide compound can be used to insure complete reaction with the triazine. The solvent or any excess acyl cyanide compound can be removed to isolate the O,O-dialkyl-N-phosphonomethyl-N-cyanomethylamide.

In reaction step (c), a mole of the amide reaction product form reaction step (b) is hydrolyzed with 5 moles of water. The hydrolysis is run in the presence of a strong acid or baseas defined above. Preferably the hydrolysis is acid-catalyzed, preferably with an inorganic acid, and most preferably with hydrochloric or hydrobromic acid. The hydrolysis yields the desired N-phosphonomethylglycine. Preferably at least 2 moles of the acid are used. More preferably, a large excess over the 2 mole amount is used. The preferred hydrochloric or hydrobromic acid can be used in concentrated or aqueous form. This last reaction step is run at a temperature between about 0° to about 200° C., preferably between about 50° to about 125° C. and most preferably between about 100° to about 125° C. Atmospheric, sub-atmospheric or super-atmospheric pressure can be used. Preferably atmospheric pressure is used during the hydrolysis.

The solid N-phosphonomethylglycine can be recovered by conventional techniques in reaction step (d). Volatile liquid products such as alcohols (methanol) chlorides (methyl chloride), acids (acetic acid), water, and excess acid can be removed by standard stripping techniques. The desired N-phosphonomethylglycine is recovered in high purity by dissolving it in water, adjusting the pH of the solution to between 1 and 2, allowing it to crystallize from solution and removing it by filtration.

The process of this invention can be better understood by reference to the following specific examples.

EXAMPLE I

Preparation of N,N',N''-Tris[O,O-diethylphosphonomethyl]hexahydrotriazine

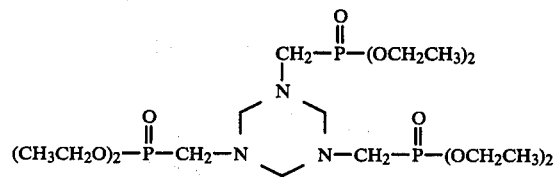

In a 50 milliliter (ml) flask, 5.1 grams (g) (0.03 mole) of O,O-diethylaminomethylphosphonate was dissolved with stirring in 15 ml of dichloromethane and cooled to 5° C. in an ice bath. Next, 3.0 g (0.03 mole) of 37% formaldehyde in 10 ml of water was added, and the mixture was stirred one hour at room temperature. Ten ml of water was added, then the aqueous layer was extracted three times with 25 ml of dichloromethane. After drying with magnesium sulfate, the solvent was evaporated to yield 5.2 g of the desired product. The structure was confirmed by proton nuclear magnetic resonance and infrared.

EXAMPLE II

Preparation of O,O-diethyl-N-phosphonomethyl-N-cyanomethyl benzamide

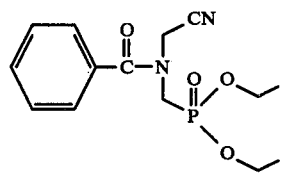

Seven tenths gram of N,N',N''-tris[O,O-diethylphosphonomethyl]hexahydrotriazine (0.0013 mole) was combined with 0.5 g (0.0038 mole) of benzoyl cyanide, 0.4 g (0.0039 mole) of 4-dimethylaminopyridine, and 5 ml of ethylene dichloride in a 50 ml flask. The solution was refluxed at 3.5 hours, then stirred at room temperature overnight. Next, 100 ml of dichloromethane was added. The organic layer was washed first with 100 ml of 0.5 molar hydrochloric acid, then with 100 ml of 5% $K_2CO_3$. Finally, the organic layer was dried and evaporated to yield 0.8 g of O,O-diethyl-N-phosphonomethyl-N-cyanomethyl benzamide. The structure was confirmed by proton nuclear magnetic resonance, infrared, and mass spectroscopy.

EXAMPLE III

Preparation of N-phosphonomethylglycine

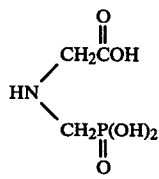

O,O-Dimethyl N-phosphonomethyl N-cyanomethyl benzamide (8.7 g, 0.0307 mole) was combined with 35 ml of concentrated hydrochloric acid in a 50 ml flask and refluxed four hours. The solution was then cooled, extracted with dichloromethane to remove benzoic acid, and the aqueous layer stripped under reduced pressure to yield 6.5 g of N-phosphonomethylglycine. The structure was confirmed by proton nuclear magnetic resonance and infrared.

What is claimed is:

1. A method of preparing N-phosphonomethylglycine comprising (a) reacting O,O-dialkylaminomethylphosphonate having the formula

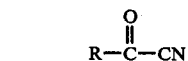

wherein $R_1$ and $R_2$ are both aromatic or aliphatic groups with at least one mole of formaldehyde at a temperature between about 0° C. to about 100° C. to produce a triazine compound of the formula

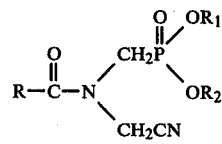

wherein $R_1$ and $R_2$ are as described above;

(b) reacting the triazine formed in step (a) with an acyl cyanide compound of the formula $$R-\overset{O}{\underset{\|}{C}}-CN$$

wherein R is an aliphatic or aromatic group at a temperature between about 0° C. to about 150° C. to form the O,O-dialkyl-N-phosphonomethyl-N-cyanomethyl amide, which has the formula wherein R, $R_1$ and $R_2$ are as defined, and (c) hydrolyzing the amide formed in step (b) in the presence of a strong acid to yield N-phosphonomethylglycine.

2. The method of claim 1 wherein R is phenyl or $C_1$-$C_4$ alkyl.

3. The method of claim 1 wherein R is phenyl or $C_1$-$C_4$ alkyl, $R_1$ is $C_1$-$C_6$ alkyl and $R_2$ is $C_1$-$C_6$ alkyl.

4. The method of claim 1 wherein R is phenyl or $C_1$-$C_4$ alkyl, $R_1$ is $C_1$-$C_4$ alkyl and $R_2$ is $C_1$-$C_4$ alkyl.

5. The method of claim 1 wherein R is phenyl or $C_1$-$C_4$ alkyl, $R_1$ is $C_1$-$C_2$ alkyl and $R_2$ is $C_1$-$C_2$ alkyl.

6. The method of claim 1 wherein R is phenyl, $R_1$ is ethyl and $R_2$ is ethyl.

7. The method of claim 1 wherein the acid is hydrochloric or hydrobromic acid.